(12) United States Patent
Kang et al.

(10) Patent No.: US 10,955,329 B1
(45) Date of Patent: Mar. 23, 2021

(54) METHOD AND SYSTEM FOR MEASURING PORE STRUCTURE OF TIGHT SANDSTONE

(71) Applicant: INSTITUTE OF GEOLOGY AND GEOPHYSICS CHINESE ACADEMY OF SCIENCES (IGGCAS), Beijing (CN)

(72) Inventors: Shujuan Kang, Beijing (CN); Yunfeng Yang, Beijing (CN); Yu Peng, Beijing (CN); Huafeng Qin, Beijing (CN); Ranran Liu, Beijing (CN); Yongxin Pan, Beijing (CN)

(73) Assignee: INSTITUTE OF GEOLOGY AND GEOPHYSICS CHINESE ACADEMY OF SCIENCES (IGGCAS), Beijing (CN)

(*) Notice: Subject to any disclaimer, the term of this patent is extended or adjusted under 35 U.S.C. 154(b) by 0 days.

(21) Appl. No.: 17/069,109

(22) Filed: Oct. 13, 2020

(30) Foreign Application Priority Data

Nov. 28, 2019 (CN) .......................... 201911188440.3

(51) Int. Cl.
- *G01N 15/08* (2006.01)
- *G01N 33/24* (2006.01)
- *G16C 60/00* (2019.01)
- *G01N 30/02* (2006.01)

(52) U.S. Cl.
CPC ....... G01N 15/088 (2013.01); G01N 15/0806 (2013.01); G01N 33/24 (2013.01); G16C 60/00 (2019.02); *G01N 15/0826* (2013.01); *G01N 2015/0833* (2013.01); *G01N 2015/0866* (2013.01); *G01N 2030/025* (2013.01)

(58) Field of Classification Search
CPC .................... G01N 15/088; G01N 2015/0866
See application file for complete search history.

(56) References Cited

U.S. PATENT DOCUMENTS

| 8,629,401 B2 * | 1/2014 | Kaskel | G01N 25/4846 |
| | | | 250/341.6 |
| 2005/0279948 A1 * | 12/2005 | Schroeder | G01N 15/088 |
| | | | 250/458.1 |

(Continued)

FOREIGN PATENT DOCUMENTS

CN 109060623 * 12/2018 ........... G01N 15/088

OTHER PUBLICATIONS

Machine translation of CN109060623A.*

*Primary Examiner* — Nathaniel J Kolb
(74) *Attorney, Agent, or Firm* — Westbridge IP LLC

(57) ABSTRACT

A method and a system for measuring the pore structure of tight sandstone are provided. The method comprises the following steps: carrying out the desorption experiment of a core sample saturated by a specific gas containing isotope element to obtain the pressure of the specific gas and the total isotope ratio at each sampling moment; acquiring a single isotope ratio of each pore diameter at each sampling moment according to a physical model containing pore diameter parameter and the pressure of the specific gas at each sampling moment; and obtaining the proportion of a pore of each pore diameter in the core sample. The method and the system for measuring the pore structure of the tight sandstone provided by the disclosure can quickly obtain the pore distribution of the tight sandstone without damaging a sample.

8 Claims, 3 Drawing Sheets

(56) References Cited

U.S. PATENT DOCUMENTS

2006/0024849 A1* 2/2006 Zhu .................. H01L 21/02137
                                                    438/12
2012/0168628 A1* 7/2012 Kaskel ............... G01N 33/2025
                                                   250/341.6

* cited by examiner

METHOD AND SYSTEM FOR MEASURING PORE STRUCTURE OF TIGHT SANDSTONE

CROSS-REFERENCE TO RELATED APPLICATIONS

The application claims priority to Chinese patent application No. 201911188440.3, filed on Nov. 28, 2019, the entire contents of which are incorporated herein by reference.

TECHNICAL FIELD

The disclosure relates to the technical field of unconventional oil and gas exploration, in particular to a method and a system for measuring the pore structure of tight sandstone.

BACKGROUND

Tight gas refers to natural gas in tight sandstone formation with permeability less than 0.1 millidarcy, which is recognized as three unconventional natural gases in the world together with shale gas and coal bed gas. Tight sandstone is the reservoir space of natural gas and the pore sizes of the tight sandstone mainly develop into nano-scale. The pore structure of the core directly affects the later reservoir reconstruction effect and the ultimate recoverable reserves. Therefore, the characterization study of the pore structure of tight sandstone has been the most basic and important work in geological research. At present, the research methods of rock pore structure include the conventional mercury intrusion method, low-temperature nitrogen adsorption method and nuclear magnetic method, each of which has its application scope. The main advantage of the mercury intrusion method is that the mercury intrusion method can be used to characterize pores from larger than 50 nm to several hundred microns. But the mercury intrusion method is a destructive experiment, low temperature nitrogen adsorption and nuclear magnetic method are usually used in the case of a small sample amount. The low-temperature nitrogen adsorption method is mostly used to study pores from 2 nm to 50 nm. Carbon dioxide is used as the adsorption gas, which can theoretically study pores as small as 0.4 nm, but cannot characterize a pore structure with a large structure. Because the pores of tight sandstone are small, the study of tight sandstone by nuclear magnetic method requires a large saturation pressure to fill water into the core, and this process is very time consuming, so that the nuclear magnetic method is uncommonly used.

SUMMARY

The technical problem to be solved by the disclosure is to provide a method and a system for measuring a pore structure of tight sandstone, which can quickly measure the pore structure of a tight sandstone and characterize the pore structures of various sizes without damaging a sample.

The disclosure is realized by the following technical scheme:

A method for measuring the pore structure of the tight sandstone. wherein the method for measuring a pore structure of tight sandstone comprises the following steps:

carrying out a gas desorption experiment of a core saturated by a specific gas to obtain the gas pressure and a total isotope value at each sampling moment, wherein the total isotope value is an isotope ratio of the specific gas flowing out from all the pores in the core sample; acquiring a single isotope ratio of each pore diameter at each sampling moment according to a physical model containing a pore diameter parameter and the pressure of the specific gas at each sampling moment, wherein the single isotope ratio is an isotope ratio of the isotope element in the specific gas flowing out of pores of a single pore diameter in the core sample; wherein the physical model containing the pore diameter parameter is a DGM (Detailed Geometric Model) model; and a proportion of a pore with each pore diameter obtained in the core sample according to $$\delta_i = \sum_{j=1}^{N} f_j \times \delta_{ij},$$

wherein $\delta_i$ is a total isotope ratio corresponding to a i sampling moment, and in i∈[1, N], N is a sampling frequency, $f_j$ is the proportion of a pore with a j pore diameter in the core sample, and $\delta_{ij}$ is a single isotope ratio of the j pore diameter corresponding to the i sampling moment.

Further, in the method for measuring a pore structure of tight sandstone, the specific gas is methane, nitrogen or carbon dioxide.

Further, in the method for measuring a pore structure of tight sandstone, the specific gas is methane, and to obtain the pressure and the total isotope ratio at each sampling moment comprises:

fixing the core sample in a core holder;
enabling the core holder to be in a vacuum state;
filling the specific gas into the core holder;
measuring the pressure of the specific gas at each sampling moment;
collecting the specific gas with preset mass at the each sampling moment;
oxidizing the collected specific gas;
and measuring the isotope ratio of the isotope element in the oxidized gas.

Further, in the method for measuring a pore structure of tight sandstone, the physical model containing pore diameter parameter is a DGM model, a Feng-Stewart model, an Arnost-Schneider model, a Shapiro model, or an Altevogt model.

Further, in method for measuring a pore structure of tight sandstone, the physical model containing pore diameter parameter is a DGM model; the specific gas is methane; the single isotope ratio of each pore diameter at the each sampling moment is obtained according to $$\delta_{ins} = \delta_0 + 1000 \left[ \ln \left( \frac{\frac{\overline{p}R^2}{8\mu} + D_K^*}{\frac{\overline{p}R^2}{8\mu} + D_K} \right) + \frac{\pi^2(D_K - D_K^*)t}{\phi R^2} \right],$$

where $\delta_{ins}$ is a single isotope ratio of a radius R corresponding to a sampling moment t, $\delta_0$ is an isotope ratio of the isotope element in the specific gas prior to the saturated core desorption experiment, $\overline{p}$ is the pressure of the specific gas corresponding to sampling time t, $\mu$ is gas viscosity, and $\phi$ is a porosity of the core sample; and in $$D_K = \frac{2R}{3}\sqrt{\frac{8R_g T}{\pi M}}, D_K^* = \frac{2R}{3}\sqrt{\frac{8R_g T}{\pi M^*}},$$

$R_g$ is an ideal gas constant, T is absolute temperature, M is the molar mass of methane containing $^{12}C$, and M* is the molar mass of methane containing $^{13}C$.

Further, in the method for measuring a pore structure of tight sandstone, before performing the desorption experiment of a specific gas-saturated core sample to obtain the pressure of the specific gas at each sampling moment, the method further comprises: measuring the porosity of the core sample.

Further, in the method for measuring a pore structure of tight sandstone, performing the desorption experiment of a specific gas-saturated core sample to obtain the pressure of the specific gas and the total isotope ratio at each sampling moment comprises:

carrying out the desorption of the core sample saturated by the specific gas, and obtaining the pressure of the specific gas and the total isotope ratio every time interval until the pressure of the specific gas does not change Further, in method for measuring a pore structure of tight sandstone, the method comprises the following steps:

a saturated core analyzing device is used for carrying out the desorption experiment of a core sample saturated by a specific gas containing isotope element to obtain the pressure of the specific gas and the total isotope ratio at each sampling moment, wherein the total isotope ratio is an isotope ratio of the isotope element in the specific gas flowing out from all pores in the core sample;

a first acquisition module is used for acquiring a single isotope ratio of each pore diameter corresponding to the each sampling moment according to a physical model containing pore diameter parameter and the pressure of the specific gas corresponding to the each sampling moment, wherein the single isotope ratio is an isotope ratio of the isotope element in the specific gas flowing out from pores with a single pore diameter in the core sample; wherein the physical model containing the pore diameter parameter is a DGM model;

a second acquisition module is used for acquiring the proportion of a pore of each pore diameter in the core sample according to $$\delta_i = \sum_{j=1}^{N} f_j \times \delta_{ij},$$

wherein $\delta_i$ is a total isotope ratio corresponding to a i sampling moment, and in i∈[1, N], N is a sampling frequency, $f_j$ is the proportion of a j pore with a pore diameter in the core sample, and $\delta_{ij}$ is a single isotope ratio of the j pore diameter corresponding to the i sampling moment.

Further, in the method for measuring a pore structure of tight sandstone, the specific gas is methane, and the saturated core analyzing device comprises:

a core holder, used for fixing the core sample;

a vacuum pump, used for enabling the core holder to be in a vacuum state;

a gas storage tank, used for storing the specific gas and filling the specific gas into the core holder;

a pressure regulating valve, used for measuring the pressure of the specific gas at each sampling moment;

a chromatographic column, used for collecting the specific gas with preset mass at each sampling moment;

an oxidation pond, used for oxidizing the collected specific gas; and an isotope spectrometer, used for measuring the isotope ratio of the isotope element in the oxidized gas.

Further, in the method for measuring a pore structure of tight sandstone, the saturated core analyzing device further comprises:

a gas cylinder, used for storing the specific gas; and a booster pump, used for pressurizing the specific gas and then filling the specific gas into the gas storage tank.

Compared with the prior art, the disclosure has the following advantages and beneficial effects.

According to the method and system for measuring the pore structure of the tight sandstone provided by the disclosure, the isotope fractionation effect in the tight sandstone with the main composition of quartz can be considered that only the isotope fractionation caused by Knudsen diffusion and viscous flow exists, and then the influence coefficient of different pore diameters on the diffusional fractionation under different pressure conditions are obtained to make the influence of the change of isotope fractionation curve be regarded as the comprehensive influence of different sizes of pores with different proportions in the tight sandstone core on fractionation, and the proportion of different pores in the core is calculated by simultaneous multi-factor equations. According to the disclosure, the saturated core desorption experiment is carried out on the core sample by adopting the specific gas. The gas molecules are small such that the whole core sample can be rapidly passed through. Meanwhile, the damage to the sample by adopting the mercury intrusion method is avoided. The method according to the disclosure can be well combined with the data generated by on-site isotope logging, and thus is innovation and supplement to the existing pore measurement method.

BRIEF DESCRIPTION OF DRAWINGS

The accompanying drawings, which are included to provide a further understanding of embodiments of the disclosure and are incorporated in and constitute a part of this application, are not to be construed as limiting the embodiments of the disclosure. In the drawings.

DETAILED DESCRIPTION OF THE EMBODIMENTS

Figure 1:
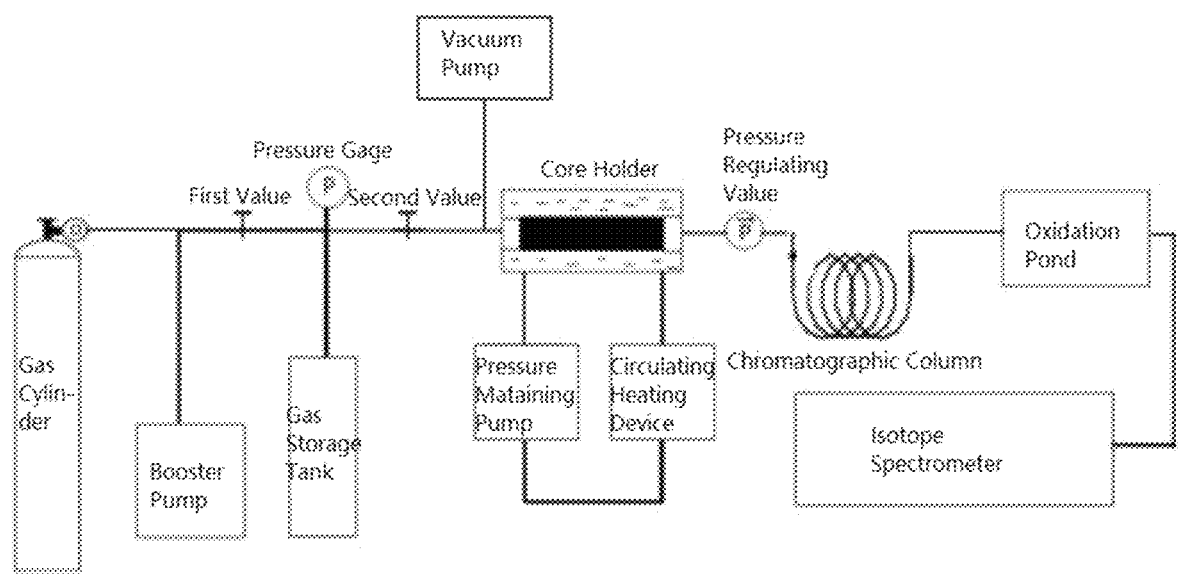
FIG. 1 is a schematic structural view of a saturated core analyzing device according to an embodiment of the present disclosure.

In order to make the objects, technical solutions, and advantages of the present disclosure clear, the present disclosure will be further described in detail below with reference to the embodiments and drawings. The exemplary embodiments of the present disclosure and the description thereof are only used to explain the present disclosure, not as a limitation of the present disclosure.

The embodiments of the disclosure provide a method for measuring a pore structure of tight sandstone, which comprises the following steps:

carrying out the desorption experiment of a saturated core sample by using a specific gas containing isotope element to obtain the pressure of the specific gas and the total isotope ratio at each sampling moment, the total isotope ratio is the isotope ratio of the isotope elements in the specific gas flowing out of all pores in the core sample;

acquiring a single isotope ratio of each pore diameter corresponding to each sampling moment according to a physical model containing a pore diameter parameter and the pressure of the specific gas corresponding to each sampling moment, the single isotope ratio is the isotope ratio of the isotope element in the specific gas flowing out of pores of single pore diameter in the core sample;

the physical model containing the pore diameter parameter is a DGM (Detailed Geometric Model) model; and obtaining the proportion of pores with each pore diameter in the core sample according to $$\delta_i = \sum_{j=1}^{N} f_j \times \delta_{ij},$$

$\delta_i$ is the total isotope ratio corresponding to the i sampling moment, and in i∈[1, N], N is the sampling frequency, $f_j$ is the proportion of pores with the j pore diameter in the core sample, and $\delta_{ij}$ is the single isotope ratio of the j pore diameter corresponding to the i sampling moment.

Specifically, the core sample is representative of the gas-producing horizon in the workspace. In this embodiment, the core sample is cylindrical. Of course, the shape and size of the core sample may be selected according to the structural parameters of the experimental device, and this embodiment is not limited thereto.

Carrying out the desorption experiment on a saturated core sample by using a specific gas containing isotope elements is to place the core sample in the specific gas and obtain the influence of pores with each pore diameter in the core sample on diffusional fractionation of the isotope elements under different pressure conditions. The specific gas may be methane containing a carbon isotope, nitrogen containing a nitrogen isotope, or carbon dioxide containing a carbon isotope. As long as gas contains an isotope element, the gas may be used as the specific gas. Different gases are used as the specific gases, and the method and the device for carrying out saturated core desorption experiments are different. Taking the specific gas as methane as an example, carrying out a methane-saturated core desorption experiment comprises the following steps: fixing the core sample in a core holder; enabling the core holder to be in a vacuum state; filling the specific gas into the core holder; measuring the pressure of the specific gas at each sampling moment; collecting the specific gas with preset mass at each sampling moment; oxidizing the collected specific gas; and measuring the isotope ratio of the isotope element in the oxidized gas.

FIG. 1 is a schematic structural diagram of a saturated core desorption device of the present embodiment including a core holder, a vacuum pump, a gas storage tank, a pressure regulating valve, a chromatographic column, an oxidation pond, and an isotope spectrometer. The core holder is used for fixing the core sample; the vacuum pump is connected with the input end of the core holder or the output end of the core holder for enabling the core holder to be in a vacuum state; the gas storage tank is connected with the input end of the core holder for storing the specific gas and filling the specific gas into the core holder; the input end of the chromatographic column is connected with the output end of the core holder for collecting the specific gas with preset mass at each sampling moment, the preset mass can be selected according to actual requirements; the pressure regulating valve is arranged between the output end of the core holder and the input end of the chromatographic column for measuring the pressure of the specific gas at each sampling moment to obtain the pressure of the specific gas corresponding to each sampling moment; the input end of the oxidation pond is connected with the output end of the chromatographic column for oxidizing the collected specific gas; and the isotope spectrometer is connected with the output end of the oxidation pond for measuring the isotope ratio of the isotope element in the oxidized gas to obtain the total isotope ratio corresponding to each sampling moment.

Since the initial pressure of the gas required to perform the saturated core desorption experiment is high, the specific gas in the gas storage tank is usually obtained by pressurizing the gas in the gas cylinder, and thus the saturated core analyzing device may further include a gas cylinder and a booster pump. The gas cylinder is connected with the gas storage tank for storing the specific gas. The booster pump is connected between the gas cylinder and the gas storage tank for pressurizing the specific gas and storing the specific gas in the gas storage tank. Further, the saturated core desorption experiment is usually performed under a constant temperature condition, and thus the saturated core analyzing device may further include a circulating heating device for performing on the core holder. The constant temperature may be room temperature or some set temperature value, which is not limited by the embodiments of the present disclosure. In addition, in order to ensure that the core holder is in a stable pressure environment, the saturated core analyzing device may further comprise a pressure maintaining pump for maintaining the pressure in the core holder.

How to perform a saturated core desorption experiment on the core sample is described in detail below with reference to FIG. 1:

opening the first valve arranged between the booster pump and the gas storage tank, closing the second valve arranged between the gas storage tank and the core holder, and injecting specific gas in the gas cylinder into the gas storage tank; in the process of injecting the specific gas into the gas storage tank, pressurizing the specific gas by using the booster pump; closing the first valve after the gas storage tank is filled with the specific gas; fixing the core sample in the core holder; after the core holder is fixed, vacuuming the core holder by using the vacuum pump to enable the core holder to be in a vacuum state; after the vacuum is pumped, opening the second valve and closing a pressure regulating valve so that the specific gas in the gas storage tank is filled into the core holder; closing the second valve after the pressure value displayed by the pressure gauge is stable, and recording the pressure value displayed by the pressure gauge the pressure value is the initial saturation pressure $P_0$ in the core holder; opening the pressure regulating valve at each sampling moment and measuring the pressure of the specific gas at each sampling moment through the pressure regulating valve to obtain the pressure of the specific gas corresponding to each sampling moment; the specific gas which passes through the pressure regulating valve entering the chromatographic column, the chromatographic column collects the specific gas with preset mass; the collected specific gas entering the oxidation pond where the oxidation pond oxidizes the specific gas, and in the embodiment, methane being oxidized to generate carbon dioxide; and the isotope spectrum being used to measure the isotope ratio of the isotope element in the oxidized gas to obtain the total isotope ratio corresponding to each sampling moment. As long as the initial saturation pressure $P_0$ does not exceed the technical parameters of the high-pressure vessel, the initial saturation pressure $P_0$ is usually 8-10 MPa. The magnitude of the initial saturation pressure $P_0$ varies for different specific gases and is not limited by this embodiment.

The time intervals between sampling moments may be the same or different. In the embodiment, when a saturated core desorption experiment is carried out on the core sample by adopting the specific gas, the pressure of the specific gas and the total isotope ratio are obtained at set time intervals until the pressure of the specific gas does not change. That is, the pressure of the specific gas and the total isotope ratio are recorded at equal time intervals until the experiment is stopped when the pressure of the specific gas is constant. The recording time is set as $t_1, t_2, t_3, t_4 \ldots$, the pressure of the specific gas corresponding to each recording time is $P_1, P_2, P_3, P_4 \ldots$, and the total isotope ratio corresponding to each recording time is $\delta_1, \delta_2, \delta_3, \delta_4 \ldots$. The length of the set time period only needs to satisfy that the gas volume of the specific gas obtained within the set time period can be subjected to isotope analysis. The length of the set time period is related to the initial saturation pressure $P_0$ and the property of the specific gas which is usually 5 to 10 minutes and is not limited in this embodiment.

Assuming that the pore diameter distribution of the core is a spherical pore with the same pore diameter interval and is combined according to a certain proportion, the isotope ratio of the isotope element is solved by adopting a physical model containing a pore diameter parameter. The isotope ratio detected at any time is a result of mixing gas flowing out of all pores of the core. According to the embodiment of the disclosure, the physical model containing the pore diameter parameter is a DGM model, and can also be other physical models containing the pore diameter parameter, such as a Feng-Stewart model, an Arnost-Schneider model, a Shapiro model or an Altevogt model and the like. Considering the gas occurrence state in the tight sandstone and the simultaneous existing Knudsen diffusion and viscous flow in nanopores, the DGM model of the spherical pore with radius $$R \text{ is } \phi \frac{\partial p}{\partial t} = \frac{1}{r^2} \frac{\partial}{\partial r} \left[ r^2 \left( \frac{\bar{p}R^2}{8\mu} + D_k \right) \frac{\partial p}{\partial r} \right],$$

$\phi$ is the porosity of the core sample, $D_k$ is the Knudsen diffusion coefficient, $\mu$ is the gas viscosity, and $\bar{p}$ is the pressure of the specific gas corresponding to the sampling time t. The flow of the methane containing $^{12}C$ and the flow of the methane containing $^{13}C$ in the cylindrical pore conform to the DGM model, namely $$\begin{cases} \phi \frac{\partial p}{\partial t} = \frac{1}{r^2} \frac{\partial}{\partial r} \left[ r^2 \left( \frac{\bar{p}R^2}{8\mu} + D_k \right) \frac{\partial p}{\partial r} \right] \\ \phi \frac{\partial p}{\partial t} = \frac{1}{r^2} \frac{\partial}{\partial r} \left[ r^2 \left( \frac{\bar{p}R^2}{8\mu} + D_k \right) \frac{\partial p}{\partial r} \right]. \end{cases}$$

The equation $$\begin{cases} p^*(t) = \frac{6}{\pi^2} \sum_{n=1}^{\infty} \frac{1}{n^2} \exp\left[ \frac{n^2\pi^2 \left( \frac{\bar{p}R^2}{8\mu} + D_K^* \right) t}{\phi R^2} \right] p_0^* \\ p(t) = \frac{6}{\pi^2} \sum_{n=1}^{\infty} \frac{1}{n^2} \exp\left[ \frac{n^2\pi^2 \left( \frac{\bar{p}R^2}{8\mu} + D_k \right) t}{\phi R^2} \right] p_0 \end{cases}$$

is obtained by solving the above equation with a spherical diffusion equation. The single isotope ratio of each pore diameter corresponding to each sampling moment can be obtained by $p(t)$ and $p^*(t)$:

$$\delta_{ins} = \delta_0 + 1000 \left[ \ln\left( \frac{\frac{\bar{p}R^2}{8\mu} + D_K^*}{\frac{\bar{p}R^2}{8\mu} + D_K} \right) + \frac{\pi^2(D_K - D_K^*)t}{\phi R^2} \right],$$

$$D_K = \frac{2R}{3} \sqrt{\frac{8R_g T}{\pi M}},$$

$$D_K^* = \frac{2R}{3} \sqrt{\frac{8R_g T}{\pi M^*}}.$$

$R_g$ is ideal gas constant, T is absolute temperature, M is the molar mass of methane containing $^{12}C$, and $M^*$ is the molar mass of methane containing $^{13}C$. The molar mass of methane containing $^{12}C$ 16 g/mol, and the molar mass of methane containing $^{13}C$ is 17 g/mol. The porosity $\phi$ of the core sample is measured before a saturated core desorption experiment is carried out, and a specific method for measuring the porosity $\phi$ of the core sample, which is not described in detail herein, can refer to the national standard GB/T 29172-2012 "Core Analysis Method".

The proportion of the pores of each pore diameter in the core sample is obtained according to $$\delta_i = \sum_{j=1}^{N} f_j \times \delta_{i,j},$$

where $\delta_i$ is the total isotope ratio corresponding to the i sampling moment, and in $i \in [1, N]$, N is the sampling frequency, $f_j$ is the proportion of pores with the j pore diameter in the core sample, and $\delta_{i,j}$ is the single isotope ratio of the j pore diameter corresponding to the i sampling moment. Solve the following system of equations:

$$\begin{cases} \delta_1 = f_1 \left\{ \delta_0 + 1000 \left[ \ln\left( \frac{\frac{p_1 d_1^2}{32\mu} + \frac{d_1}{3}\sqrt{\frac{8R_g T}{\pi M^*}}}{\frac{p_1 d_1^2}{32\mu} + \frac{d_1}{3}\sqrt{\frac{8R_g T}{\pi M}}} \right) + \frac{\pi^2 t_1 \sqrt{T}}{25\phi d_1} \right] \right\} + \ldots + f_N \left\{ \delta_0 + 1000 \left[ \ln\left( \frac{\frac{p_1 d_N^2}{32\mu} + \frac{d_N}{3}\sqrt{\frac{8R_g T}{\pi M^*}}}{\frac{p_1 d_N^2}{32\mu} + \frac{d_N}{3}\sqrt{\frac{8R_g T}{\pi M}}} \right) + \frac{\pi^2 t_1 \sqrt{T}}{25\phi d_N} \right] \right\} \\ \delta_N = f_1 \left\{ \delta_0 + 1000 \left[ \ln\left( \frac{\frac{p_N d_1^2}{32\mu} + \frac{d_1}{3}\sqrt{\frac{8R_g T}{\pi M^*}}}{\frac{p_N d_1^2}{32\mu} + \frac{d_1}{3}\sqrt{\frac{8R_g T}{\pi M}}} \right) + \frac{\pi^2 t_N \sqrt{T}}{25\phi d_1} \right] \right\} + \ldots + f_N \left\{ \delta_0 + 1000 \left[ \ln\left( \frac{\frac{p_N d_N^2}{32\mu} + \frac{d_N}{3}\sqrt{\frac{8R_g T}{\pi M^*}}}{\frac{p_N d_N^2}{32\mu} + \frac{d_N}{3}\sqrt{\frac{8R_g T}{\pi M}}} \right) + \frac{\pi^2 t_N \sqrt{T}}{25\phi d_N} \right] \right\}. \end{cases}$$

Where $d_1, \ldots, d_N$ is a diameter corresponding to each pore in the core sample. Isotope fractionation is based on the difference in the probability of collision between light carbon methane and heavy carbon methane in the nanopore and the pore wall which results in the difference in diffusion rate. The smaller the pore diameter is, the more obvious the fractionation is. Thus, the isotope fractionation method mainly measures a micropore and a small mesopore. Therefore, the initial pore diameter $d_1$ of the core sample can be selected to be small. The pore diameter interval is determined according to experimental data and calculation requirement: the more experimental data, the higher the pore diameter characterization requirement; conversely, the smaller the experimental data, the lower the pore diameter characterization requirement, and a large interval can be selected. The $f_1, f_2, f_3, f_4, \ldots, f_N$ obtained by solving the above equation is the proportion of the pores with the diameter of $d_1, d_2, d_3, d_4, \ldots, d_N$ in the core sample.

Figure 2:
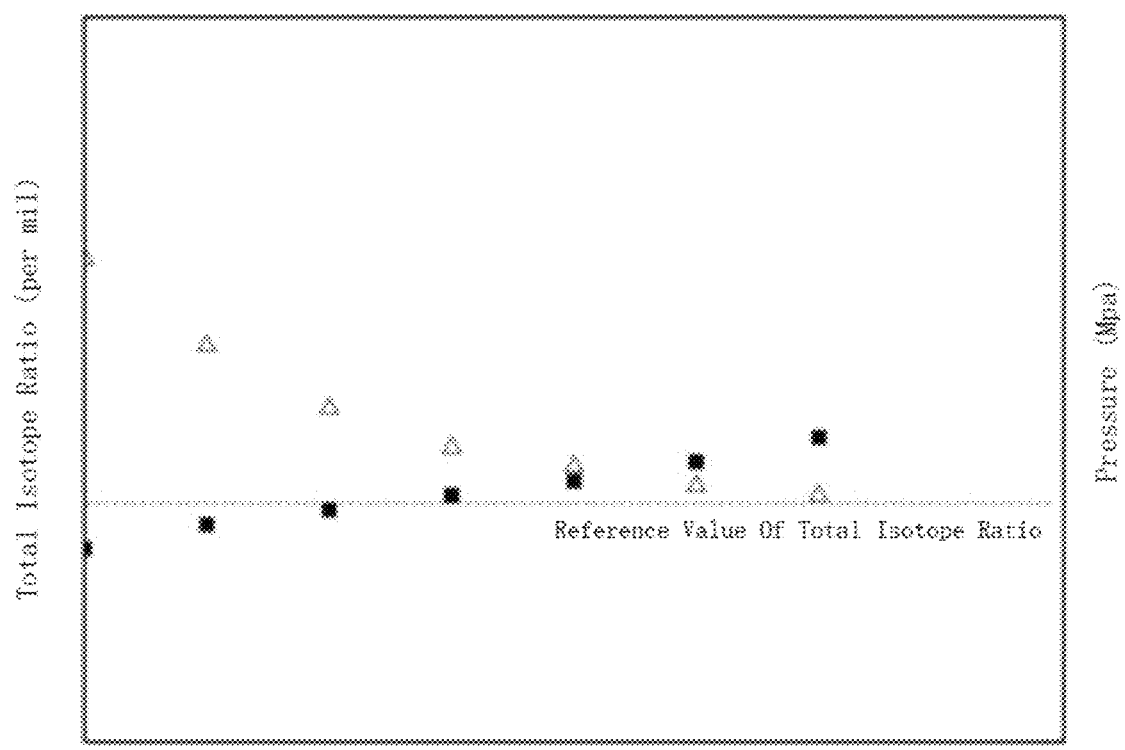
FIG. 2 is a data diagram of a saturated core desorption experiment according to an embodiment of the present disclosure.

The scheme is illustrated by a specific embodiment as follows:

a core column sample which can represent the gas-producing horizon of the area was obtained in the working area, and the porosity of the sample was determined to be 6.3%;

the core was cut into 3 cm length; the gas storage tank was filled with 13 MPa of methane by the device shown in FIG. 1; the saturation pressure in the core holder was controlled to be 10 MPa by the second valve, the isotope ratio of the carbon in experimental methane was −30‰ and the experimental temperature was 300K at room temperature;

the methane flowing from a core holder with a saturation pressure of 10 MPa entered the oxidation pond through a chromatographic column, the temperature of the oxidation pond being 850° C. where the methane was oxidized into carbon dioxide; the isotope ratio of the carbon in the carbon dioxide was measured by an isotope spectrometer; experimental data were recorded every 5 minutes for a total of 6 hours, and 72 data points were recorded, and a sample point time t, a pressure p of the methane in the core holder, and the isotope ratio $\delta$ of carbon were recorded as shown in FIG. 2;

a total of 72 characteristic pore diameter values, denoted as $d_2, d_5, d_8, \ldots, d_{215}$, with 2 nm as the initial diameter of the tight sandstone and 3 nm increasing at equal intervals were obtained; the corresponding proportion of each pore diameter was denoted as $f_2, f_5, f_8, \ldots, f_{215}$; and the known experimental parameter was substituted into the expression of the single isotope ratio of each pore diameter corresponding to each sampling moment obtained by the DGM model to obtain the following formula:

$$\delta_{ins} = -30 + 1000 \left[ \ln \left( \frac{\frac{\bar{p}d^2}{32\mu} + 6.44d}{\frac{\bar{p}d^2}{32\mu} + 6.64d} \right) + \frac{108.43t}{d} \right].$$

Combined with the experimental data, the following simultaneous equations can be established:

$$\begin{cases} \delta_1 = f_2 \left\{ 30 + 1000 \left[ \ln \left( \frac{\frac{p_1 d_2^2}{32\mu} + 6.44 d_2}{\frac{p_1 d_2^2}{32\mu} + 6.64 d_2} \right) + \frac{108.43 t_1}{d_2} \right] \right\} + \ldots + f_{215} \left\{ -30 + 1000 \left[ \ln \left( \frac{\frac{p_1 d_{215}^2}{32\mu} + 6.44 d_{215}}{\frac{p_1 d_{215}^2}{32\mu} + 6.64 d_{215}} \right) + \frac{108.43 t_1}{d_{215}} \right] \right\} \\ \delta_{72} = f_2 \left\{ 30 + 1000 \left[ \ln \left( \frac{\frac{p_{72} d_2^2}{32\mu} + 6.44 d_2}{\frac{p_{72} d_2^2}{32\mu} + 6.64 d_2} \right) + \frac{108.43 t_{72}}{d_2} \right] \right\} + \ldots + f_{215} \left\{ -30 + 1000 \left[ \ln \left( \frac{\frac{p_{72} d_{215}^2}{32\mu} + 6.44 d_{215}}{\frac{p_{72} d_{215}^2}{32\mu} + 6.64 d_{215}} \right) + \frac{108.43 t_{72}}{d_{215}} \right] \right\}. \end{cases}$$

Figure 3:
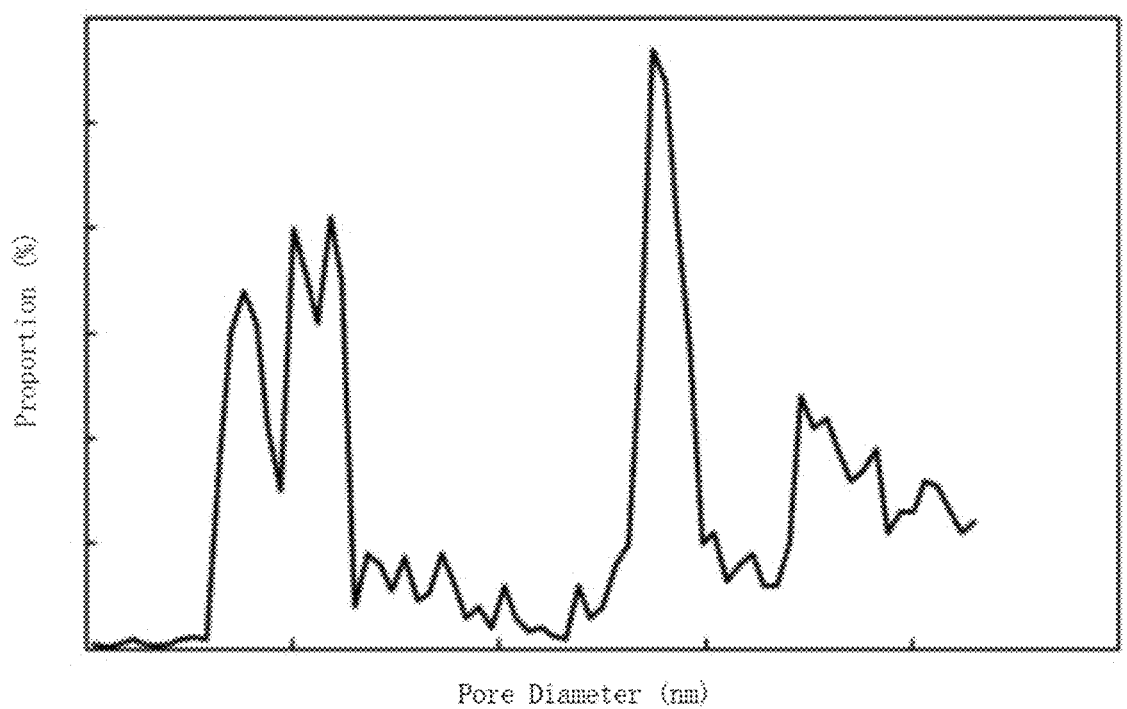
FIG. 3 is a pore diameter distribution diagram of a tight sandstone according to an embodiment of the present disclosure.

From the solution of the above equations, $f_2, f_5, f_8, \ldots, f_{215}$ were solved, and the pore diameter distribution of the core was obtained as shown in FIG. 3.

According to the method for measuring the pore structure of the tight sandstone provided by the embodiment, the isotope fractionation effect in the tight sandstone with the main composition of quartz can be considered that only the isotope fractionation caused by Knudsen diffusion and viscous flow exists, and then the influence coefficient of different pore diameters on the diffusional fractionation under different pressure conditions are obtained to make the influence of the change of isotope fractionation curve be regarded as the comprehensive influence of different sizes of pores with different proportions in the tight sandstone core on fractionation, and the proportion of different pores in the core is calculated by simultaneous multi-factor equations. According to the embodiment, the saturated core desorption experiment is carried out on the core sample by adopting the specific gas. The gas molecules are small such that the whole core sample can be rapidly passed through. Meanwhile, the damage to the sample by adopting the mercury intrusion method is avoided. The method according to the disclosure can be well combined with the data generated by on-site isotope logging, and thus is innovation and supplement to the existing pore measurement method.

Based on the same inventive concept, the disclosure also provides tight sandstone pore structure measurement system, which comprises the following steps:

a saturated core analyzing device is used for carrying out the desorption experiment of a core sample saturated by a specific gas containing isotope element to obtain the pressure of the specific gas and the total isotope ratio at each sampling moment, the total isotope ratio is the isotope ratio of the isotope element in the specific gas flowing out from all pores in the core sample;

a first acquisition module is used for acquiring a single isotope ratio of each pore diameter at each sampling moment according to a physical model containing pore diameter parameter and the pressure of the specific gas at each sampling moment, the single isotope ratio is the isotope ratio of the isotope element in the specific gas flowing out from pores with a single pore diameter in the core sample;

the physical model containing the pore diameter parameter is a DGM model;

a second acquisition module is used for acquiring the proportion of the pores of each pore diameter in the core sample according to $$\delta_i = \sum_{j=1}^{N} f_j \times \delta_{i,j}, \delta_i$$

is the total isotope ratio corresponding to the i sampling moment, and in i∈[1, N], N is the sampling frequency, $f_j$ is the proportion of pores with the j pore diameter in the core sample, and $\delta_{ij}$ is the single isotope ratio of the j pore diameter corresponding to the i sampling moment.

In an alternative implementation, the specific gas is methane, nitrogen or carbon dioxide.

In an alternative implementation, the specific gas is methane, and the saturated core analyzing device comprises:

a core holder, used for fixing the core sample;

a vacuum pump, used for enabling the core holder to be in a vacuum state;

a gas storage tank, used for storing the specific gas and filling the specific gas into the core holder;

a pressure regulating valve, used for measuring the pressure of the specific gas at each sampling moment;

a chromatographic column, used for collecting the specific gas with preset mass at each sampling moment;

an oxidation pond, used for oxidizing the collected specific gas; and an isotope spectrometer, used for measuring the isotope ratio of the isotope element in the oxidized gas.

In an alternative implementation, the saturated core analyzing device further comprises:

a gas cylinder, used for storing the specific gas; and a booster pump, used for pressurizing the specific gas and then filling the specific gas into the gas storage tank.

In an alternative implementation, the physical model containing the pore diameter parameter is a DGM model, a Feng-Stewart model, an Arnost-Schneider model, a Shapiro model, or an Altevogt model.

In an alternative implementation, the physical model containing the pore diameter parameter is a DGM model, the specific gas is methane and the single isotope ratio of each pore diameter corresponding to each sampling moment is obtained according to $$\delta_{ins} = \delta_0 + 1000 \left[ \ln \left( \frac{\frac{\bar{p}R^2}{8\mu} + D_K^*}{\frac{\bar{p}R^2}{8\mu} + D_K} \right) + \frac{\pi^2(D_K - D_K^*)t}{\phi R^2} \right],$$

where $\delta_{ins}$ is the single isotope ratio of the radius R corresponding to the sampling time t, $\delta_0$ is the isotope ratio of the isotope element in the specific gas prior to the saturated core desorption experiment, $\bar{p}$ is the pressure of the specific gas corresponding to the sampling time t, $\mu$ is the gas viscosity, and $\phi$ is the porosity of the core sample. In $$D_K = \frac{2R}{3} \sqrt{\frac{8R_g T}{\pi M}},$$

$$D_K^* = \frac{2R}{3} \sqrt{\frac{8R_g T}{\pi M^*}},$$

$R_g$ is the ideal gas constant, T is the absolute temperature, M is the molar mass of methane containing $^{12}C$, and M* is the molar mass of methane containing $^{13}C$.

In an alternative implementation, the tight sandstone pore structure measurement system further comprises:

a porosity measuring device, used for measuring the porosity of the core sample.

In an alternative implementation, the saturated core analyzing device obtains the pressure of the specific gas and the total isotope ratio at set intervals until the pressure of the specific gas does not change.

The working principle of the measurement system for the pore structure of the tight sandstone is similar to the method for measuring the pore structure of the tight sandstone, which is not described in detail herein.

The objects, technical solutions, and advantages of the present disclosure have been described in further detail with reference to the above-described preferred embodiments, and it is to be understood that the above description is only illustrative of the preferred embodiments of the disclosure and is not intended to limit the scope of the disclosure. Any modification, equivalent replacement, improvement, etc., made within the spirit and principle of the present disclosure shall be included in the protection scope of the present disclosure.

What is claimed is:

1. A method for measuring the pore structure of tight sandstone, comprising the following steps:

carrying out a desorption experiment of a core sample saturated by a specific gas containing an isotope element to obtain a pressure of a specific gas and a total isotope ratio at each sampling moment, wherein the total isotope ratio is an isotope ratio of the isotope element in the specific gas flowing out of all pores in the core sample;

wherein carrying out a desorption experiment comprises the steps of:

fixing a core sample in a core holder;

enabling the core holder to be in a vacuum state;

filling a specific gas into the core holder;

measuring the pressure of the specific gas at each sampling moment;

collecting the specific gas with preset mass at each sampling moment; and oxidizing the collected specific gas;

acquiring a single isotope ratio of each pore diameter at each sampling moment according to a physical model containing a pore diameter parameter and the pressure of the specific gas at each sampling moment, wherein the single isotope ratio is an isotope ratio of the isotope element in the specific gas flowing out of pores of single pore diameter in the core sample;

wherein the physical model containing the pore diameter parameter is a DGM (Detailed Geometric Model) model; and a proportion of a pore with each pore diameter is obtained in the core sample according to $$\delta_i = \sum_{j=1}^{N} f_j \times \delta_{ij},$$

wherein $\delta_i$ is a total isotope ratio corresponding to an i sampling moment, and in i∈[1, N], N is a sampling frequency, $f_j$ is the proportion of a j pore with a pore diameter in the core sample, and $\delta_{ij}$ is a single isotope ratio of the pore diameter corresponding to the i sampling moment.

2. The method for measuring a pore structure of tight sandstone according to claim 1, wherein the specific gas is methane, nitrogen or carbon dioxide.

3. The method for measuring a pore structure of tight sandstone according to claim 1, wherein the physical model containing pore diameter parameter is a DGM model; the specific gas is methane; the single isotope ratio of each pore diameter corresponding to each sampling moment is obtained according to $$\delta_{ins} = \delta_0 + 1000 \left[ \ln \left( \frac{\frac{\bar{p}R^2}{8\mu} + D_K^*}{\frac{\bar{p}R^2}{8\mu} + D_K} \right) + \frac{\pi^2 (D_K - D_K^*) t}{\phi R^2} \right],$$

where $\delta_{ins}$ is a single isotope ratio of a radius R corresponding to a sampling moment t, $\delta_0$ is an isotope ratio of the isotope element in the specific gas prior to the saturated core desorption experiment, $\bar{p}$ is the pressure of the specific gas corresponding to sampling time t, $\mu$ is gas viscosity, and $\phi$ is a porosity of the core sample; and in $$D_K = \frac{2R}{3} \sqrt{\frac{8R_g T}{\pi M}},$$

$$D_K^* = \frac{2R}{3} \sqrt{\frac{8R_g T}{\pi M^*}},$$

$R_g$ is an ideal gas constant, T is absolute temperature, M is the molar mass of methane containing $^{12}C$, and M* is the molar mass of methane containing $^{13}C$.

4. The method for measuring a pore structure of tight sandstone according to claim 3, wherein before adopting the specific gas containing isotope element to perform a saturated core desorption experiment on a core sample to obtain the pressure of the specific gas and the total isotope ratio at each sampling moment, the method further comprises:

measuring the porosity of the core sample.

5. The method for measuring a pore structure of tight sandstone according to claim 1, wherein performing a saturated core desorption experiment to obtain the pressure of the specific gas and the total isotope ratio at each sampling moment comprises:

carrying out the desorption experiment of the core sample saturated by a specific gas, and obtaining the pressure of the specific gas and the total isotope ratio at set intervals until the pressure of the specific gas does not change.

6. A system for measuring the pore structure of tight sandstone, comprising:

a saturated core analyzing device, used for carrying out the desorption experiment of a core sample saturated by a specific gas containing isotope element to obtain a pressure of the specific gas and a total isotope ratio at the each sampling moment, wherein the total isotope ratio is an isotope ratio of the isotope element in the specific gas flowing out from all pores in the core sample; wherein the saturated core analyzing device comprises:

a core holder, used for fixing the core sample;

a vacuum pump, used for enabling the core holder to be in a vacuum state;

a gas storage tank, used for storing the specific gas and filling the specific gas into the core holder;

a pressure regulating valve and pressure gauge, used for measuring the pressure of the specific gas at each sampling moment;

a chromatographic column, used for collecting the specific gas with preset mass at each sampling moment;

an oxidation pond, used for oxidizing the collected specific gas; and an isotope spectrometer, used for measuring the isotope ratio of the isotope element in the oxidized gas;

a first acquisition module, used for acquiring a single isotope ratio of each pore diameter at each sampling moment according to a physical model containing a pore diameter parameter and the pressure of the specific gas at the each sampling moment, wherein the single isotope ratio is an isotope ratio of the isotope element in the specific gas flowing out from pores with a single pore diameter in the core sample; wherein the physical model containing the pore diameter parameter is a DGM model;

a second acquisition module is used for acquiring the proportion of a pore of each pore diameter in the core sample according to $$\delta_i = \sum_{j=1}^{N} f_j \times \delta_{ij},$$

wherein $\delta_i$ is a total isotope ratio corresponding to an i sampling moment, and in i∈[1, N], N is a sampling frequency, $f_j$ is the proportion of a pore with a j pore diameter in the core sample, and $\delta_{ij}$ is a single isotope ratio of the j pore diameter corresponding to the i sampling moment.

7. The system for measuring a pore structure of tight sandstone according to claim 6, wherein the specific gas is methane.

8. The system for measuring a pore structure of tight sandstone according to claim 7, wherein the saturated core analyzing device further comprises:
   a gas cylinder, used for storing the specific gas; and
   a booster pump, used for pressurizing the specific gas and then filling the specific gas into the gas storage tank.

* * * * *